(12) United States Patent
Lamon et al.

(10) Patent No.: US 7,387,125 B2
(45) Date of Patent: Jun. 17, 2008

(54) CONTROLLED EXTRICATION MODULE FOR MOTOR VEHICLE CRASH INJURED PEOPLE

(76) Inventors: Marcelo Fernando Lamon, Virrey del Pino N° 2336, Tablade Park CP(5000) Córdoba (AR); Agustín Lascano Garzon, San José de Calasans N° 43-2do "B", Córdoba (AR) CP 5000; Ernesto Aliaga Paz, General Bustos 545, Tanti-Córdoba (AR) CP 5155

( * ) Notice: Subject to any disclaimer, the term of this patent is extended or adjusted under 35 U.S.C. 154(b) by 477 days.

(21) Appl. No.: 10/318,928

(22) Filed: Dec. 13, 2002

(65) Prior Publication Data

US 2003/0140927 A1 Jul. 31, 2003

(30) Foreign Application Priority Data

Dec. 17, 2001 (AR) ............................. M010105849

(51) Int. Cl.
*A61F 5/37* (2006.01)
(52) U.S. Cl. ...................................... 128/846; 128/869
(58) Field of Classification Search ......... 128/845–846, 128/869–876; 5/630, 636, 638, 640
See application file for complete search history.

(56) References Cited

U.S. PATENT DOCUMENTS

| | | | | |
|---|---|---|---|---|
| 3,707,734 A * | 1/1973 | Matthews | ...................... | 5/628 |
| 3,889,668 A * | 6/1975 | Ochs et al. | ................... | 128/870 |
| 5,027,833 A * | 7/1991 | Calkin | ........................ | 128/870 |
| 5,724,992 A * | 3/1998 | Ip | .............................. | 128/845 |
| 6,223,749 B1 * | 5/2001 | Beaty | ......................... | 128/869 |
| 6,318,372 B1 * | 11/2001 | Hiebert | ....................... | 128/869 |
| 6,467,486 B1 * | 10/2002 | Kleinschmidt | .............. | 128/869 |
| 6,772,764 B2 * | 8/2004 | Chapman | .................... | 128/870 |

* cited by examiner

*Primary Examiner*—Michael A. Brown
(74) *Attorney, Agent, or Firm*—Bachman & LaPointe

(57) ABSTRACT

A controlled extrication module for the injured composed of a body with several means of immobilization of an injured person and supplied with devices for handling, maneuvering and transporting. The module is composed of a rigid plaque that provides a rear part with a medium zone coinciding with a person's back, a lower zone coinciding with a sacrococcygeal zone, and an upper zone coinciding with neck and head. The upper zone has a rounded edge which coincides with a cranial base and a border enabling attachment to an upper end of a seat. The upper zone also has two cavities for placing cervical collar straps which delimit a central help and semi-rigid fins connected to additional straps which attach at their ends. Both sides of the medium zone have upper and lower projections and an intermediate space supplying a side border. The border is placed on a side edge of the seat. The module also has a harness made up of upper and lower strips. The plaque lower zone is provided with two belts and a number of hand-holds.

10 Claims, 2 Drawing Sheets

CONTROLLED EXTRICATION MODULE FOR MOTOR VEHICLE CRASH INJURED PEOPLE

BACKGROUND OF THE INVENTION

This invention consists of a controlled extrication module for people injured in motor vehicle crashes.

In order to understand this invention so that it can be easily put into practice, a detailed description of the recommended implementation and drawings will be given in the following paragraphs. The description purpose is purely demonstrative and does not set limits to the invention itself whose components could be selected among several equivalents without neglecting the invention principles stated in this documentation.

One of the main problems in motor vehicle crashes is removing the injured trapped inside the vehicle.

This situation gets worse when people trying to help do not have first aid training.

In fact, people trying to assist the victims in a vehicle crash frequently cause more severe injuries than the ones they are trying to reduce.

Reduced reaction time when accelerating and stopping modern vehicles give the user more versatility in driving; however, motor vehicle accidents are more severe every time.

Although most motor vehicles have safety devices to reduce the impact resulting from a crash, such as safety cage deformation, safety belts, and air bags amongst others, these safety devices do not guarantee zero trauma injuries due to the nature of the accidents that occur.

In such accidents, spine injuries are a frequent consequence as a result of muscle tension weakening the vertebrae, in most of the cases, as well as compressions, side movements, etc. resulting from the vehicle crash itself.

Similarly, significant collapse of the vehicle structure and high speed cause fractures, fissures, luxations, and even explosion of vertebrae. Since these injuries are close to the medullar duct, they may result in the victim having permanent mobilization difficulties.

Taking into account, as stated before, that many of the injuries resulting from motor vehicle crashes are due to displacement of the medullar duct of the vertebrae effected while moving the victim's head, neck or spine, different devices have been designed with the aim of reducing injuries.

In fact, the well known cervical collar or Philadelphia collar has been designed to be used to immobilize head and neck position in relation to the spine.

Another device for reducing injuries is the rigid backboard supplied with body and head straps as well as side handles making patient transportation easier for the rescuers.

An extrication vest used to immobilize the patient while performing rescue and patient transport operations is also well known.

The wraparound design of the extrication vest provides flexibility and allows for thorax, head, and neck immobilization.

Standard extrication vests are generally supplied with hand-holds which make application as well as patient transportation safer, and with colored-coded straps for easy application as well as for getting X-rays and receiving first aid, without taking off the extrication vest.

Such extrication vests adapt for children and pregnant women and may be used as hip splints. They are also easy to fold and manipulate.

However, as required in some of the procedures described, it is necessary to move, and in some cases to remove, the victim in order to use or apply the extrication device.

SUMMARY OF THE INVENTION

In order to develop the present invention, the inventor has considered that such movements, even when carried out by medical experts, present a risk with severe consequences.

Also, the inventor has taken into consideration the fact that it is sometimes impossible to use some of the devices mentioned above without moving the patient.

The inventor has also considered that thoracic-abdominal injuries have increased geometrically in relation to population and the number of vehicles during the last years.

The inventor has also taken into account the fact that in some vehicles, like those prepared for competition, rescue maneuvers are difficult to perform since competition vehicles usually have welded doors, side bars, and a safety cage for the driver and in some cases for a passenger.

Added to those elements, oil pan, spare equipment, tools, and electronic equipment reduce the available space for rescue maneuvers. The greatest difficulty for the rescuers is presented mainly by the competition seat.

The inventor has taken into consideration the fact that there may be situations where it would not be convenient to use a priori the module described.

The inventor is aware that medical contraindication for using any kind of extrication vest is hemothorax or pneumothorax, likely to be found in some injured persons.

However, the inventor considers that such contraindication is relative and depends basically on how quickly and easily the vest can be applied.

Considering the peculiarities of the present invention, the inventor thinks that given the technique and required knowledge, even when the patient suffers from dyspnea type III, the use of the module is preferable.

In fact, although applying the present invention would compress the patient thorax, its use may be limited to the minimum required to remove the victim from the vehicle, since the damage caused by the module would be insignificant compared to the importance of keeping the victim's spine safe.

The inventor thinks that if the trauma is severe enough to cause thorax injures, it is highly probable that the patient has spinal injury too, so once the patient is removed from the vehicle, straps can be loosened and the module taken off if required.

Under this circumstance, the victim's pathology, that is thorax injury, can be treated without any risk of further spinal injury since the patient's spine would be immobilized.

If as a result of using the present invention shortness of breath increases due to strap compression and the patient's hypoxia is accentuated, such risks are minimal as compared to medullar injury sequelae. Besides, it is reversible applying the proper treatment, that is pleural drainage, oxygen-therapy, etc.

Due to the facts described before, it can be concluded that vehicle crash incidents may cause spinal injuries and that immediate spine immobilization is a preferred solution in order to avoid irreversible sequelae.

For this reason, the purpose of the present invention, which consists of a controlled extrication module for the injured, is to provide a rigid module adapted to contain the thoracicoabdominal zone of a person.

Another purpose of the present invention is to keep the patient's spine safe during extrication and transportation of the patient by means of the extrication module, reducing the risk of further aggravating injuries when performing rescue and transport operations.

It is also a purpose of the present invention to firmly apply the above mentioned module, providing a means of body immobilization to the person who uses it.

Also, another purpose of the present invention is to provide a secure means of handling to facilitate patient transportation to the rescue teams.

A further purpose of the present invention is to include the extrication module to the driver or passenger vehicle seat.

BRIEF DESCRIPTION OF THE DRAWINGS

The illustration sheet shows in

DETAILED DESCRIPTION OF THE PREFERRED EMBODIMENTS

Figure 1:
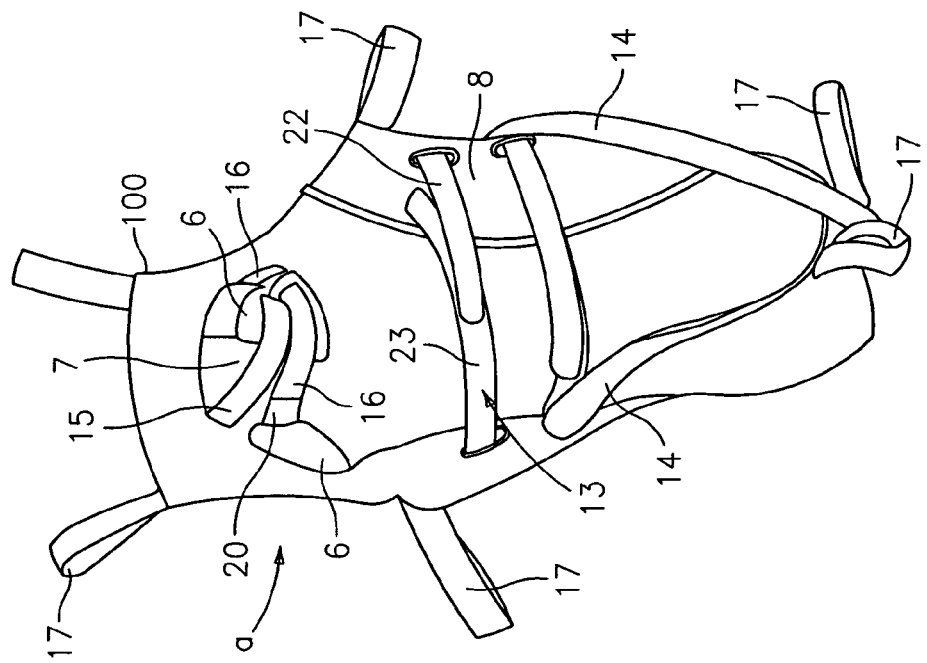
FIG. 1, a perspective view of the seat with the semi-rigid plaque that constitutes the extrication module of the present invention.

In the above described figures, the same reference numbers indicate equal or corresponding parts as follows: reference number (1) refers to a middle zone of the extrication module (100); reference number (2) refers to a lower zone of the extrication module (100); reference number (3) refers to an upper zone of the extrication module (100) and reference number (4) refers to a rounded edge of the extrication module (100).

Reference number (5) indicates a seat on which the extrication module (100) is positioned. Reference number (6) indicates a pair of cavities in the extrication module (100). Reference number (7) indicates a center help associated with a cervical collar (20). Reference number (8) indicates a side aid.

Reference number (9) indicates an upper projection of the extrication module (100). Reference number (10) indicates a lower projection of the extrication module (100). Reference number (11) is a side border of the extrication module and reference number (12) is a side edge of the seat (5).

Reference number (13) indicates a harness. Reference number (14) indicates a belt. Reference number (15) indicates semi-rigid fins used to secure a patient's head and reference number (16) indicates straps which are used, along with a cervical collar (20 to secure a patient's neck.

Finally, reference number (17) indicates handles and letter (a) indicates the semi-rigid plaque that constitutes the extrication module.

Basically, the present invention provides a rigid plaque (a) which is ergonomically adapted to the thoracicoabdominal zone and supplied with hand-holds (handles (17)) as well as immobilization devices for the legs, trunk, neck, and head of the injured.

Such a rigid plaque is preferably included in the vehicle seat.

Having established the different components of this invention version, a functional and operative relation to the invention components, as well as their results, are now described.

In order to obtain a controlled extrication module (100) for the injured, a rigid plaque (a) is required which provides a proper design to place the thoracicoabdominal zone of a person.

The plaque (a) has a rear part with a middle zone (1) which coincides with the patient's back, a lower zone (2) which covers the sacrococcygeal zone of the patient, and an upper zone (3) which coincides with the neck and head of the patient.

The upper zone (3) has a rounded edge (4) which coincides with the cranial base of the patient and has a border which enables it to be attached onto the upper edge of the seat (5) so as to secure both devices together.

The upper zone (3) has two cavities (6) for placing a cervical collar (20) and straps (16) situated on both sides of a center help (7), thus providing neck support as well as a means against which the cervical collar (20) performs compression force.

The front portions of the cervical collar straps (16) provide a secure connection while allowing adjustment and securing of the patient's neck. In the middle zone (1), side aids (8) wrap around the thorax, with an upper projection (9) at the level of the patient's shoulders and a lower projection (10) at the level of the patient's abdomen, leaving an intermediate space for allowing mobility of the patient's arm.

Between the upper (9) and lower (10) projections, there is a side border (11) situated on the side edge (12) of the seat (5) in order to secure the connection of the seat (5) to the plaque (a).

On both plaque sides, there is a harness (13) made up of upper (22) and lower (23) straps that, when the extrication module is used, allows for immobilization of the thoracicoabdominal zone of the injured person or patient.

Finally, the plaque lower zone (2) has two belts (14) for providing immobilization of the groin area.

With the foregoing devices, an injured person is firmly attached to the plaque (a) by four points.

The head is secured by a cervical collar formed by both semi-rigid fins (15) which are placed on the frontoparietal zone and whose ends may be connected by straps (not shown) to fasten the forehead.

Figure 2:
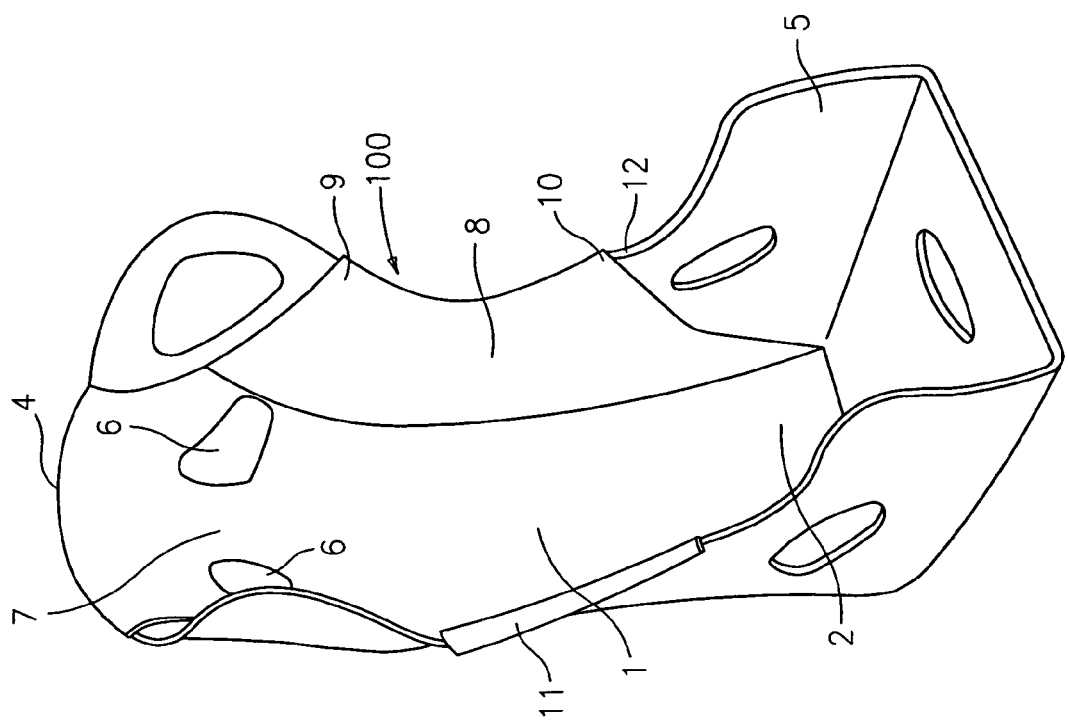
FIG. 2 shows a perspective view of the extrication module detached from the seat, in a different scale.
Figure 3:
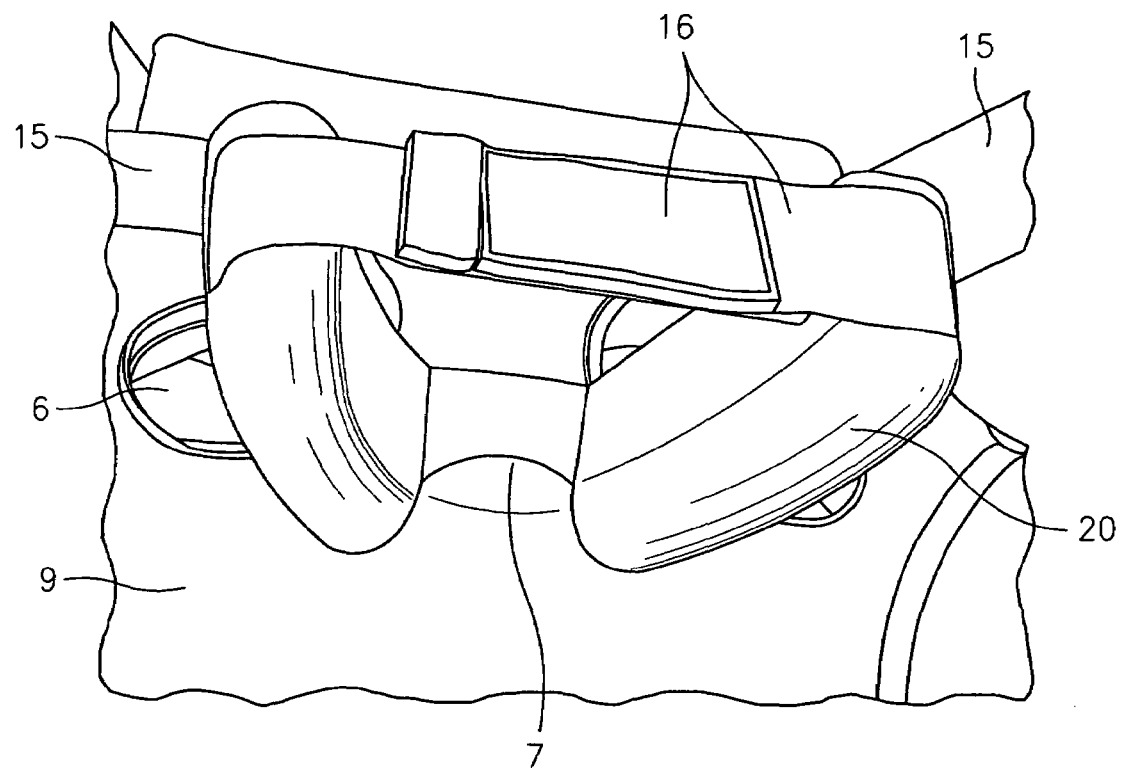
FIG. 3 illustrates a cervical collar and semi-rigid fins used to clamp a patient's head and neck.

The neck is secured by a cervical collar (20) attached to the center help (7) and by straps (16) as shown in FIGS. 2 and 3.

The thoracicoabdominal zone is secured by the harness (13) and the thighs are secured by the belts (14).

In order to facilitate extrication and transportation of the patient, the plaque (a) has a number of hand-holds (17) that are made of a resistant material like the type of material used for safety belts.

The described extrication module (100) made up of the plaque (a) and the securing devices can be used with any vehicle seat (5) and the plaque size and form can be adapted to the seat size and form.

For this reason, the manufacturers of such seats (5) will be in charge of the manufacture of the extrication module, thus enabling its location in different ways.

However, manufacturers may choose to press the plaque (a) against the back of the vehicle seat (5) and then to fill the inside and tapestry in order to keep the original seat design.

In specific places of the seat (5), the ends of the harness (13), belts (14), fins (15), cervical collar (20), and hand-holds (17) will be in place for allowing prompt and efficient rescue operations just by pulling and adjusting the straps to fit and immobilize patients.

Thus, for such vehicles, a way to make efficient the utilization of the module which is the object of the present invention is to construct the plaque (a) of an appropriate material with a design suitable for the seat design.

The upper area of the plaque (a) is articulated and joined to the seat headrest where the cervical collar is fitted into.

Both semi rigid fins (15) are situated under the cervical collar (20) and if necessary, they are rotated and placed on the frontoparietal zone of the patient, then both ends are joined and adjusted firmly on the patient's forehead.

Harness (13) designed to immobilized the thoracicoabdominal zone are fitted under the seat tapestry on both sides, in the kidney zone, because it is a very accessible location for rescue teams and also because it does not alter the original design of the vehicle seat (5).

The lower part of the seat (5) has belts (14) used to immobilize the groin area, with an end connected to the plaque (a) and the other end placed at the front of the seat.

It would be necessary that four, and preferably six, hand-holds (17) are applied for immobilizing the module once it has been adjusted to the patient during rescue procedures.

At least one of the hand-holds (17) should be placed in the seat headrest, two of them in the dorsolumbar zone on both sides and finally, a longer one in the coxal zone crossing the seat that will be placed in the front area of the seat.

On the contrary, in some vehicles, like competition cars, which are more exposed to incidents, it is preferred that the occupants are in direct contact with the plaque (a) attached to the seat (5) by means of a quick release buckle (not shown).

Mainly in competition cars, the module can be equipped with different kinds of medical instruments, like a pulse meter, that can be applied to the harness (13) in order to check, constantly and promptly, the patient's cardiac condition.

It is also convenient to have an oxygen mask and an oxygen pipe under the seat (5) for dispnea cases.

In the case of a car crash, the procedure for applying the module (100) is very simple. The steps to follow vary according to the position of the crashed vehicle.

If the crashed vehicle remains on its four wheels, safety belts should be released first and, the cervical collar (20) should be adjusted second. If the patient is wearing a helmet, it is not necessary to remove it since the cervical collar (20) allows for adjustment with a helmet on.

Next, the harness (13) should be adjusted firstly by the upper straps across the thorax, secondly by the lower straps across the abdomen, and finally by the belts (14) for fastening the groin area.

Finally, the plaque (a) should be detached from the seat (5) by releasing the buckles to remove the injured person.

In the case that the crashed vehicle is on one of its sides or upside down, the above stated procedures should be followed but beginning from the second step and then releasing the safety belts in the last step in order to avoid the risk that the patient falls from the seat aggravating the injuries the patient may have.

It is important to point out that by incorporating the extrication module into vehicle seats, the injured could be released more promptly, thus getting them to the medical facilities in better physical and psychological conditions and improving recovery possibilities.

Once the patient is fixed to the module (100), the patient has to be extricated by slowly rotating the module (100). Legs should be extricated first, then by holding the hand-holds (17), with the help of another person, the patient should be extricated and placed on a backboard.

As a preferred way of making the plaque (a), it is made of a thin plate of fiber and Kevlar material.

In such a preferred way of manufacture, the module is covered with a cloth material in order to avoid skinning by direct body contact with the plaque (a), and at the same time to provide a finish appealing to the sight.

In this way we have concluded presenting the purpose of this invention and its way of functioning. The documentation is accompanied by the invention synthesis stated in the following claims.

The invention claimed is:

1. An extrication module for the injured for use with a vehicle seat, said module comprising:
    a rigid plaque that provides a rear part with a middle zone coinciding with a person's back, a lower zone coinciding with a person's sacrococcygeal zone, and an upper zone coinciding with a person's neck and head;
    said upper zone having a border enabling attachment to an upper end of said seat;
    said upper zone having two cavities for placing cervical collar straps situated on both sides of a center help and for placing semi-rigid fins;
    said middle zone having an intermediate space supplying a side border;
    said side border being placed on a side edge of the seat;
    a harness;
    said lower zone being provided with a plurality of belts;
    a plurality of hand holds; and
    semi-rigid fins which are placed on a frontoparietal zone of the person and connected by straps.

2. The extrication module of claim 1, wherein an upper part of the rigid plaque is uniformly articulated.

3. The extrication module of claim 2, further comprising a cervical collar.

4. The extrication module of claim 1, wherein the upper zone border is positioned at shoulder level, a lower border is positioned at abdomen level, and the intermediate space allows for arm mobility.

5. The extrication module of claim 1, wherein the belts in the lower zone comprise belts for immobilization of a groin zone of the person.

6. The extrication module of claim 1, wherein the hand-holds are made up of a resistant material of the kind used for safety belts.

7. The extrication module of claim 1, wherein the plaque is made up of a thin plate of fiber and KEVLAR material.

8. The extrication module according to claim 1, wherein said upper zone has a rounded edge.

9. The extrication module according to claim 1, wherein each side of said module having an upper projection and a lower projection.

10. An extrication module for the injured for use with a vehicle seat, said module comprising:
    a rigid plaque that provides a rear part with a middle zone coinciding with a person's back, a lower zone coinciding with a person's sacrococcygeal zone, and an upper zone coinciding with a person's neck and head;
    said upper zone having a border enabling attachment to an upper end of said seat;
    said upper zone having two cavities for placing cervical collar straps situated on both sides of a center help and for placing semi-rigid fins;
    said middle zone having an intermediate space supplying a side border;
    said side border being placed on a side edge of the seat;
    a harness;
    said lower zone being provided with a plurality of belts;
    a plurality of hand holds;
    an upper part of the rigid plaque being uniformly articulated;
    a cervical collar; and
    semi-rigid fins which are placed on a frontoparietal zone of the person and connected by straps.

* * * * *